United States Patent [19]

Latham

[11] Patent Number: 4,660,552
[45] Date of Patent: Apr. 28, 1987

[54] RESTRAINING DEVICE FOR SPINAL TAPS

[76] Inventor: Philip B. Latham, 384 Oldham Ave., Lexington, Ky. 40502

[21] Appl. No.: 650,535

[22] Filed: Sep. 14, 1984

[51] Int. Cl.$^4$ ............................................. A61F 13/00
[52] U.S. Cl. ..................................... 128/134; 269/328
[58] Field of Search ................. 128/134, 133, 135, 94, 128/DIG. 15, 78, 80 R; 119/96; 296/328, 322

[56] References Cited

U.S. PATENT DOCUMENTS

| | | | |
|---|---|---|---|
| 1,860,874 | 5/1932 | Triplett | 128/134 |
| 3,271,028 | 9/1966 | Albin | 269/328 X |
| 3,358,141 | 12/1967 | Hoffmann et al. | 128/134 X |
| 3,829,079 | 8/1974 | Fox | 269/328 |
| 3,984,093 | 10/1976 | Pretlow, III | 269/328 |
| 4,000,736 | 1/1977 | Bruscemi | 128/80 R |
| 4,223,670 | 9/1980 | Cramer | 128/134 |
| 4,391,438 | 7/1983 | Heffington . | |

OTHER PUBLICATIONS

Olympic Lumbarstraint, Olympic Medical, 4400 Seventh South, Seattle, Wash. 98108.

*Primary Examiner*—Mickey Yu
*Attorney, Agent, or Firm*—Oblon, Fisher, Spivak, McClelland & Maier

[57] ABSTRACT

A restraining device for patients who are undergoing a spinal tap procedure. A frame is shaped like an inverted V. The patient sits on one side of the frame with his knees over the apex and his feet on the other side. His head is placed between his knees and his wrists extend near his ankles. One adjustable belt fits around his waist. Another belt holds his neck. An adjustable bar carries belt loops to hold both ankles and wrists. The patient is held from moving by the belts yet is not uncomfortable during the procedure.

6 Claims, 5 Drawing Figures

4,660,552

RESTRAINING DEVICE FOR SPINAL TAPS

BACKGROUND OF THE INVENTION

1. Field of the Invention

This invention relates generally to a restraining device and more particularly to a comfortable yet effective restraining device for spinal taps.

2. Description of the Prior Art

In the practice of medicine, it is often desirable to have the patient immobile so that he is not harmed during a dangerous procedure. One method of immobilization that is commonly used is a restraint, that is, an immovable object to which the patient is strapped or otherwise connected. Many forms of restraints have been designed for various types of procedures. Their design depends largely on the type of movement which must be prevented and the parts of the body involved.

One procedure that is somewhat dangerous to the patient is the spinal tap. A needle must be inserted between two vertebra in the lumbar region of the back in order to withdraw spinal fluid from the spinal canal. Once the needle is inserted, any movement by the patient could cause the needle to come into contact with the spinal cord and cause serious and perhaps irreparable damage to the patient.

When this procedure must be used on small children, the danger is even more prevalent. Being frightened by the unfamiliar environment and unable to understand the nature of the procedure, the child will often squirm or fight to get away. In addition to this movement, there also occur involuntary reactions to pain just as in an adult patient.

In order to prevent any movement during the procedure, the patient, especially if a child, is physically held down by nurses or other medical personnel. If the patient is fighting the procedure, a great deal of force may be necessary in order to hold him immobile. The patient is then uncomfortable and if small runs the risk of damage from the forceful holding.

Various forms of restraints have been designed for use in spinal surgery or other spinal procedures. Examples of these are shown in U.S. Pat. Nos. 4,223,670, 4,391,438 and 3,829,079. Other restraints such as shown in U.S. Pat. No. 4,000,736 may be used for restraining other parts of the body. However these and other similar restraints suffer from the problems of being expensive, difficult to operate, not adjustable and uncomfortable for the patient.

SUMMARY OF THE INVENTION

Accordingly, one object of this invention is to provide a novel restraint for a spinal tap which holds the patient immobile.

Another object of this invention is to provide a spinal tap restraint which is comfortable for the patient yet renders him immobile.

A further object of this invention is to provide a restraint which is adjustable to the size of the patient and easy to operate.

A still further object of this invention is to provide a spinal tap restraint which is inexpensive, easy to operate and comfortable to use.

Briefly, these and other objects of the invention are achieved by providing a frame having an inverted V shape. A strap on one side of the frame holds the waist of the patient in place. A strap over the apex of the V holds the neck of the patient. An adjustable bar on the other side of the frame carries straps to hold the patient's wrists and ankles and may be moved according to the patient's height.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
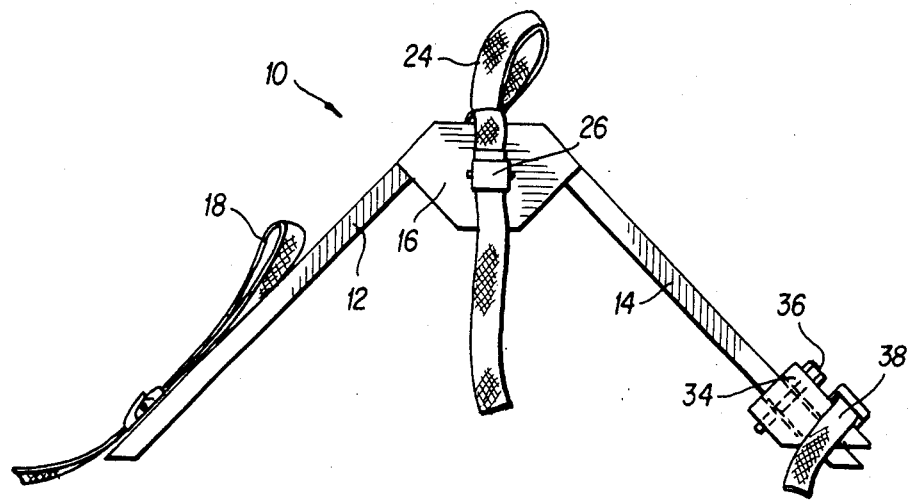
FIG. 1 is a side elevational view of the present invention.

Referring now to the drawings, wherein like reference numerals designate identical or corresponding parts throughout the several views, and more particularly to FIG. 1 thereof, where a side view of the instant invention is shown as including a frame generally indicated by 10. The frame is generally the shape of an inverted V having a front surface piece 12, a rear surface piece 14 and an apex piece 16.

Figure 2:
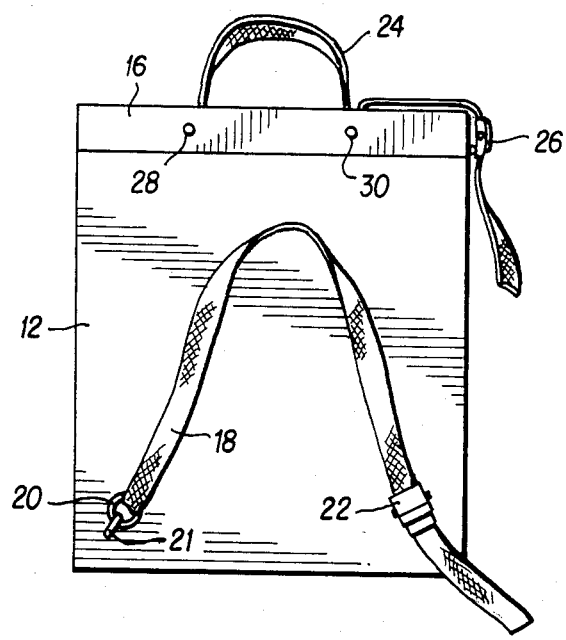
FIG. 2 is a front elevational view of the present invention.

As shown in FIG. 2, the front surface piece 12 carries a waist belt 18. One end of the belt is connected to a ring 20 which is connected to the surface piece by a screw eye 21 or similar connector. The ring and belt end may move around the screw eye freely but not away from it.

The other end of belt 18 is pulled through a buckle 22. The buckle is mounted to the surface piece by means of a screw eye (not shown) or in a similar manner so that the buckle is held to the surface but is manuverable. The buckle may be of any suitable construction, but is preferably of the friction roller type which allows continuous adjustment and requires no holes in the belt.

A neck belt 24 is carried by apex piece 16. The end of the belt is placed in a slot (not shown) in the apex piece and connected to pin 28. This pin is located parallel to the surface of the apex piece and does not extend above the front or rear surfaces, so as not to be a hazard to the patient.

After forming a loop for receiving the patient's neck, belt 24 enters a second slot (not shown) and passes under a second pin 30 before exiting on top of the apex piece. The belt then travels along the flat upper surface of the apex piece and over the end of the apex piece. A buckle 26 is mounted on the end of the apex piece in a similar manner to that of buckle 22. The end of belt 24 is placed through buckle 26.

Figure 3:
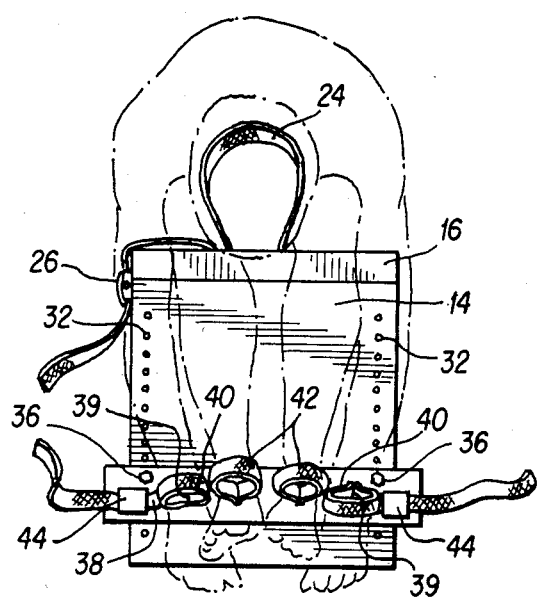
FIG. 3 is a rear elevational view of the present invention.

FIG. 3 shows the rear surface piece 14 with a row of holes 32 along the side edges. An adjustable bar 34 may be placed in various positions on the surface piece by means of pins 36 which pass through the bar and into the holes. By removing the pins and moving the bar over holes closer to or farther from the apex piece the bar may be moved up or down the surface piece.

The bar carries an ankle and wrist belt 38 along the length of the bar. Two buckles 44 are mounted on the upper surface of the bar, near either end. The buckles are mounted in a manner similar to the other buckles. The belt extends from the buckles inwardly along the upper surface of the bar until slots 39 are reached. The belt passes through the slot and then extends along the bottom surface of the bar. Additional slots are formed in the bar so that the belt may pass up through one slot and down through an adjacent slot to form a loop. Four such sets of slots form two wrist loops 40 and two ankle loops 42.

In operation, the patient sits on the front surface piece 12 with thighs resting on this surface. The knees extend over the apex piece 16. The calves rest on the rear surface piece 14. Adjustable bar 34 is moved up or down the rear surface by placing the pins 36 in holes 32 so that the ankles may be placed through the loops 42. Waist belt 18 is then passed through buckle 22 and tightened.

Neck belt 24 is placed over the neck of the patient and tightened in buckle 26 as he puts his head between his knees. The arms then are extended parallel to and outside the legs along the rear surface. The wrists are placed in loops 40 of belt 38. Both ends of the belt are tightened by buckles 44 so as to fit firmly around the ankles and wrists.

Once in this position, the patient finds himself firmly secured so that he can make neither voluntary nor involuntary movements. Although he is restrained, there is no pressure on any part of the body and the position he has assumed is relatively comfortable. The lumbar part of the spine is fully exposed so that the spinal tap is easily performed. Since the procedure itself takes usually only 2-4 minutes, the patient does not get tired in this position. Upon completion of the procedure, the buckles are released and the patient may remove himself from the belts.

The surface pieces of the invention may be made from wood, for example ¾ inch plywood, which has sufficient strength to hold the weight of the patient. The apex piece may be made from heavier material such as a 4×4, in order to have sufficient strength and size to make the connections to the surface pieces. The frame pieces could be made of lighter material if a steel frame or similar strength members were included under the surface pieces. Also, a bar or cable could be placed between the surface pieces near their bottom to avoid spreading of the frame. The frame could also be hinged near the apex to allow the frame to fold up for storage. Material other than wood could be used for the surface pieces. For example, metal, fiberglass or plastic could be used.

The angle at the apex is preferably about 90°, but could be any angle which is comfortable for the patient. The top of the apex piece should be flat and wide enough to carry the neck belt without slipping off. If desired, the top and other surfaces could be padded for the comfort of the patient.

Other types of belt holders may be used in place of the buckles. For example, Velcro holders may be placed on the belts. Two buckles are preferred on the adjustable bar, since it would be difficult to tighten all four loops securely from one end. However, it would be possible to have one buckle with the other end permanently fastened. It would also be possible to have two belts, either one for each side or separate belts for ankles and wrists with one or two buckles per belt.

It is convenient to fasten both wrists and ankles to the same adjustable board rather than requiring separate boards for each. Nature has cooperated in this by making bodily proportions appropriately sized. However, it also is possible to use separate boards if desired for any reason, for example, where the patient has very short legs.

Where the belt passes through slots in the various pieces to form loops, it is possible to use instead a flat bracket or staple under which the belt may pass. However, care must be taken that their placement will not harm the patient.

The pin arrangement for holding the adjustable bar in position may be replaced by any holding mechanism which firmly holds the bar in place. For example, the pin and hole arrangement may be replaced by a slide track and tightening screw, a clamp arrangement or a form of eccentric cam.

Figure 4:
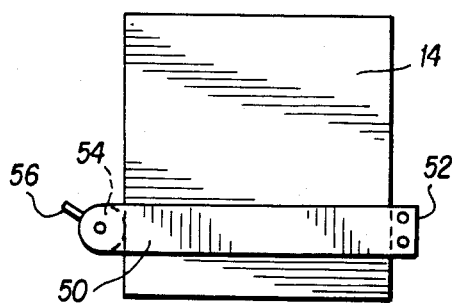
FIG. 4 is a rear elevational view of a second embodiment of the present invention.
Figure 5:
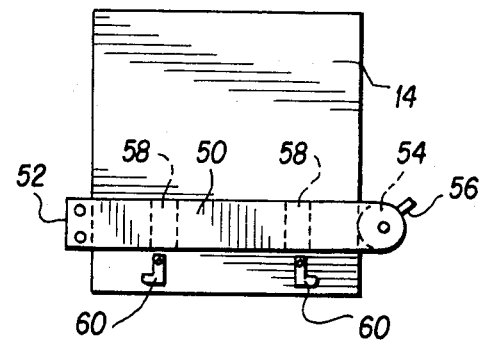
FIG. 5 is an elevational view of the back side of the rear surface piece of a second embodiment of the present invention.

FIGS. 4 and 5 show one example of such an eccentric cam arrangement. Bar 50 corresponds to adjustable bar 34 shown in the other figures and carries wrist and ankle belts (not shown) as in the other embodiment. On one end of the bar, a block 52 slides along one edge of the rear surface and prevents the bar from moving to the left. At the other end of the bar is eccentric cam 54.

The cam is mounted for rotation on the end of the bar, but not at the center of the cam. Thus, when the cam is rotated, the edge of the cam comes into contact with the edge of the rear surface, thus preventing bar 50 from moving. If desired, the cam or edge of the rear surface may carry a resilient but non-slip surface such as rubber to prevent damage to the parts from tightening the cam too tight and also to prevent the cam from sliding on the surface.

The cam may include a handle 56 or similar mechanism to rotate the cam.

FIG. 5 shows the back side of bar 50 where two vertical channels 58 are formed. Also, two L shaped brackets 60 are nailed to the back of the rear surface so that the brackets are pivotable. When the brackets are at their lowest position, the channels 58 fit over the vertical parts of the brackets, while the horizontal parts catch the bottom edge of the bar to prevent it from sliding off the rear surface piece. When it is desired to remove the bar, the brackets are swung up so that both parts of the L fit through the channel.

Obviously, numerous additional modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A restraining device for a patient undergoing medical treatment comprising:
   a frame having the shape of an inverted V including a front planar surface piece and a rear planar surface piece joined together along one edge of each planar surface piece to form an apex of the inverted V;
   a waist belt attached to said front planar surface piece;
   a bar extending across the width of said rear planar surface piece and being adjustable along the height of said rear planar surface piece;
   a wrist and ankle belt mounted on said bar;

wherein the waist of said patient is held by said waist belt and the wrists and ankles of said patient are held by said wrist and ankle belt so that said patient may not move during said medical treatment.

2. A restraining device according to claim 1 further comprising:
   a neck belt attached to said frame near said apex;
   wherein the neck of said patient is held by said neck belt during said medical treatment.

3. A restraining device according to claim 1 further comprising:
   an apex piece joining said front planar surface piece and said rear planar surface piece.

4. A restraining device according to claim 2 further comprising:
   at least one adjustable fastening device for each of said waist belt, said neck belt and said wrist and ankle belt.

5. A restraining device according to claim 1 further comprising:
   bar adjusting means including at least one pin which passes through apertures in said bar and said rear planar surface piece to hold said bar from moving.

6. A restraining device according to claim 1 further comprising:
   bar adjusting means including an eccentric cam mounted on said bar to hold said bar from moving.

* * * * *